United States Patent

DeLuca et al.

[11] 4,229,359
[45] Oct. 21, 1980

[54] DERIVATIVES OF 25-HYDROXYCHOLECALCIFEROL

[75] Inventors: Hector F. DeLuca; Heinrich K. Schnoes; Yoko Tanaka, all of Madison; Joseph B. Alper, Waunakee, all of Wis.

[73] Assignee: Wisconsin Alumni Research Foundation, Madison, Wis.

[21] Appl. No.: 71,973

[22] Filed: Sep. 4, 1979

[51] Int. Cl.² ............................................ C07J 9/00
[52] U.S. Cl. ........................ 260/397.2; 260/239.55 R
[58] Field of Search ..................................... 260/397.2

[56] References Cited

U.S. PATENT DOCUMENTS

| | | | |
|---|---|---|---|
| 4,028,349 | 6/1977 | Partridge, Jr. et al. | 260/397.2 |
| 4,038,272 | 7/1977 | Partridge, Jr. et al. | 260/397.2 |

OTHER PUBLICATIONS

Steroids, Nov. 1978, vol. 32, No. 4, pp. 453–465.

*Primary Examiner*—Elbert L. Roberts
*Attorney, Agent, or Firm*—Howard W. Bremer

[57] ABSTRACT

Compounds having the structure

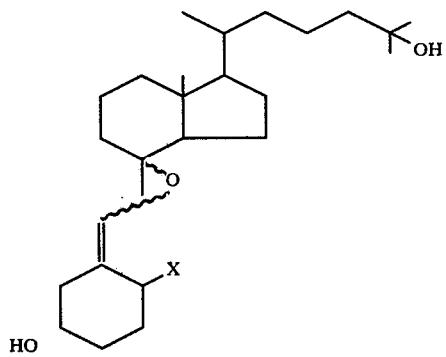

where X is keto or hydroxy.

The compounds display vitamin D like activity and would find appliction in disease states characterized by adverse calcium-phosphorous balance or behavior.

2 Claims, No Drawings

DERIVATIVES OF 25-HYDROXYCHOLECALCIFEROL

The invention described herein was made in the course of work under a grant or award from the Department of Health, Education, and Welfare.

DESCRIPTION

1. Technical Field

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin is first hydroxylated in the liver to form 25-hydroxy vitamin $D_3$ and is further hydroxylated in the kidney to produce $1\alpha,25$-diphydroxy vitamin $D_3$ or $24,25$-dihydroxy vitamin $D_3$. The $1\alpha$-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

2. Background Art

References to various of vitamin D derivatives are extant in the patent and other literature. See, for example, U.S. Pat. Nos. 3,565,924 directed to 25-hydroxycholecalciferol; 3,697,559 directed to 1,25-dihydroxycholecalciferol; 3,741,996 directed to 1α-hydroxycholecalciferol; 3,907,843 directed to 1α-hydroxyergocalciferol; 3,715,374 directed to 24,25-dihydroxycholecalciferol; 3,739,001 directed to 25,26-dihydroxycholecalciferol; 3,786,062 directed to 22-dehydro-25-hydroxycholecalciferol; 3,847,955 directed to 1,24,25-trihydroxycholecalciferol; 3,906,014 directed to 3-deoxy-1α-hydroxycholecalciferol; 4,069,321 directed to the preparation of various side chain fluorinated vitamin $D_3$ derivatives and side chain fluorinated dihydrotachysterol$_3$ analogs.

Disclosure of Invention

A new derivative of vitamin $D_3$ has now been found which expresses excellent vitamin D-like activity and which, therefore, could serve as a substitute for vitamin $D_3$ in its various known applications and would be useful in the treatment of various diseases such as osteomalacia, osteodystrophy and hypoparathyroidism. This derivative is $3\beta,25$-dihydroxy-7,8-epoxy-19-nor-9,10-secocholest-5-en-10-one, represented by structure I below.

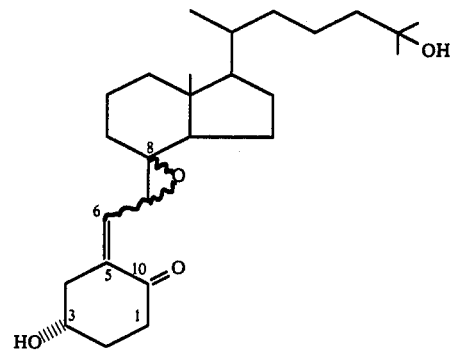

Best Mode for Carrying Out the Invention

The new vitamin D derivative (compound I) was produced from 25-hydroxycholecalciferol (25-hydroxyvitamin $D_3$). In vitro incubation of 25-hydroxycholecalciferol with a kidney homogenate yielded a mixture of products from which the desired vitamin derivative, the compound of structure I above, was isolated and purified by chromatography. The compound was structurally characterized by its spectrochemical properties.

The preparation, isolation and characterization of this novel vitamin D derivative is more fully described by the examples below.

EXAMPLE 1

Preparation of Kidney Homogenate and Incubation Media

Five male albino rats, 150–175 g each, were decapitated and the kidneys were removed. A 5% (w/v) kidney homogenate was prepared in cold 0.25 M sucrose; using a Teflon/glass tissue homogenizer. The homogentate was centrifuged at 8000×g for 15 minutes; the supernatant was decanted and saved.

A buffer solution was prepared that consisted of potassium phosphate buffer, pH 7.4, 200 mM; glucose-6-phosphate, 22.4 mM; ATP, 20 mM; nicotinamide, 160 mM; and NADP, 0.40 mM. The pH was readjusted to 7.4 with 2 N KOH.

A salt solution was prepared consisting of 5 mM $MgCl_2$, 100 mM KCl, and 10 units of glucose-6-phosphate dehydrogenase in 20 ml of distilled water.

EXAMPLE 2

Incubation of 25-hydroxycholecalciferol with Kidney Homogenate

Five ml of homogenate supernatant, 2.5 ml of buffer, and 2.5 ml of salt solution (all prepared as described above) were combined in a 125 ml Erlenmeyer flask. This mixture was flushed with $O_2$ for 30 seconds. Three hundred micrograms of 25-hydroxyvitamin $D_3$ in 100 μl of ethanol was then added and the flask was capped. Thirty such flasks were prepared and were incubated for two hours with shaking (120 oscillations per minuted) at 37° C. The contents of the flasks were then poured into 1500 ml of dichloromethane in a 2 liter separatory funnel; the flasks were rinsed once with dichloromethane. The resulting biphasic mixture was agitated for five minutes, followed by removal of the organic phase. The remaining aqueous phase was reextracted with 1500 ml dichloromethane. The combined organic phases were then concentrated in vacuo to ca. 100 ml, and this solution was refrigerated overnight. The resulting precipitate was removed by filtration and the solvent was removed in vacuo.

EXAMPLE 3

Isolation and Purification of Product

Evaporation of the dichloromethane extract (as obtained in Example 2) left a yellow oil, which was dissolved in 0.5 ml of chloroform/hexane (65/35, v/v) and chromatographed on a 0.7×14 cm Sephadex LH-20 column packed in the same solvent. The first 11 ml of eluant was discarded and the next 25 ml was collected. The solvent was removed in vacuo and the resulting oil was dissolved in 0.5 ml hexane/chloroform/methanol (9/1/1). This was chromatographed on a 0.7×15 cm Sephadex LH-20 column, packed in and developed with hexane/chloroform/methanol, 9/1/1 (Sephadex LH-20 is a hydroxypropyl ether derivative of a polydextran marketed by Pharmacia Fine Chemicals Inc., Piscataway, N.J.). The first 9 ml of eluant was discarded and the next 20 ml was collected; the solvents were removed in vacuo to give a clear oil.

The clear oil was dissolved in 150 μl of 9% 2-propanol/hexane and chromatographed on a 4.6×250 mm Zorbax-SiL (a product of Dupont Co., Wilmington, Delaware) straight phase high pressure liquid chromatograph column fitted on a Model ALC/GPC-204 liquid chromatograph (Waters Associates, Milford, Mass.); eluant was monitored for absorbance at 254 nm. The solvent system, 9% 2-propanol/hexane at a flow rate of 1.5 ml/min, eluted the desired product (compound I above) between 48–51 ml. After evaportion of the solvent, the sample was redissolved in 150, μl methanol/water, 70/30. This was chromatographed on a 9.4×250 mm Zorbax-ODS (octadecylsilane bonded to silia beads available through the Dupont Co., Wilmington, Delaware) reversed phase high pressure liquid chromatograph column using methanol/water, 70/30 as the eluant at a flow rate of 2.0 ml/min. The desired product (compound I) eluted between 151–153 ml; these fractions were collected and solvent evaporated under a stream of nitrogen. The compound was redissolved in 100 μl of 9% 2-propanol/hexane and was rechromatographed as above. This gave pure product.

Characterization of Product

The UV absorption spectrum of the product in absolute methanol exhibited a $\lambda_{max}=256$ nm and a $\lambda_{min}=212$ nm. This indicated that the vitamin D triene chromphore had been modified. When the UV spectrum was taken in ether, the $\lambda_{max}$ was shifted to 263 nm. Such a bathochromic shift is characteristic of an $\alpha,\beta$ unsaturated ketone.

The high resolution mass spectrum of the compound exhibited a molecular ion at m/e 418.3128, corresponding to the molecular formula $C_{26}H_{42}O_4$. Since the molecular formula of the precursor, 25-hydroxyvitamin $D_3$, is $C_{27}H_{44}O_2$, the mass spectral results indicated the loss of a methylene group and addition of two oxygens. The prominent peaks at m/e 138.0674 ($C_8H_{10}O_2$, representing the A ring plus C-6 and C-7), and m/e 120.0598 (138-$H_2O$) indicate the addition of one oxygen atom and the loss of one methylene unit in ring A of the molecule. U.V. and mass spectral data therefore suggest the replacement of the 10,-19 methylene unit by a 10-keto function. The presence of C-25 and C-3-hydroxy groups is indicated by peaks of m/e 59 (base peak $C_3H_7O$, due to C-25,26,27+oxygen) and m/e 120 (loss of C-3-OH from ring A fragment).

The high resolution nuclear magnetic resonance spectrum of the product (270 MHz in $CDCl_3$) exhibited a one-proton doublet at δ6.43 ppm, J=10 Hz, assigned to an olefinic proton; no other olefinic resonances were observed. In particular, the two singlets at δ5.94 and δ5.3 due to the two C-19 protons, and the doublet at δ5.94 representing the C-7 proton in the precursor, 25-hydroxycholecalciferol were absent confirming the replacement of the C-19 methylene group by a ketone function. A one-proton doublet at 3.76 ppm (J=10 Hz) can be assigned to the proton of an oxirane ring system. Decoupling experiments established spin-spin coupling between the protons at 6.43 and 3.76 ppm and thus the presence of a double bond adjacent to the expoxide function. The downfield shift of the δ6.43 peak indicates that it is the $C_\beta$ proton of an $\alpha,\beta$ unsaturated ketone, i.e., the C-6 proton. Thus the δ3.76 resonance must be due to a single proton on C-7. Because no other changes were seen upon decoupling the C-7 proton, C-8 must be fully substituted. The presence of a 25-hydroxy function is confirmed by the six-proton singlet at δ1.28 and the C-3α-carbinyl proton multiplet at δ3.95 establishes the C-3-hydroxy function. These data therefore require a 10-keto-5,6-en-7,8-epoxide system, and the combination of spectral results cited establish formula I above as the structure of this novel vitamin D derivative.

As a final confirmation of this structure, the compound was reduced with sodium borohydride to yield the corresponding 10-hydroxy compound; the product was purified by thin layer chromatography. The UV spectrum absorption was characterized by the replacement of a $\lambda_{max}$ at 252 with a weak absorption at 230 nm, indicative of the weak chromophore of an $\alpha,\beta$ unsaturated epoxide. The 10-hydroxy compound would be characterized by biological activity equivalent to the 10-keto compound.

Biological Activity

Male rats (Holtzman Co., Madison, WI) were housed in wire cages and given food and water ad libitum for 4 weeks. They were fed a low-calcium vitamin D-deficient diet described by Suda et al (J. Nutr. 100, 1049–1050, 1970). The rats were then divided into three groups of 7–9 animals each and dosed intrajugularly with the test substances. One group received 0.1 ml of ethanol (negative control group), the second received 1,25-dihydroxycholecalciferol (1,25-$(OH)_2D_3$) in 0.1 ml ethanol (positive control group) and the third received the new vitamin D derivative (compound I) in 0.1 ml of ethanol. Amounts are indicated in the table below. Twenty-four hours after dosing, the rats were killed, their blood was collected and their small intestine was removed.

Bone calcium mobilization activity was assayed by measuring the rise in serum calcium levels in response to test compound administered. The collected blood was centrifuged, and a 0.1 ml aliquot of the serum obtained was diluted with 1.9 ml of a 0.1% lanthanum chloride solution. Serum calcium concentrations were determined with an atomic absorption spectrometer Model 403 (Perkin-Elmer Corporation, Norwalk, Conn.). Results are tabulated below.

Intestinal calcium transport activity was determined by a modification of the technique of Martin and DeLuca (*Arch. Biochem. Biophys.* 134, 139–148, 1969).

Results are tabulated below.

| Compound Administered | Ca transport activity μmoles $^{45}$Ca transported/ cm$^2$ intestine (number of animals) | Serum Ca mg/100 ml (number of animals) |
| --- | --- | --- |
| 0.1 ml ethanol | 82.3 ± 15.6 (9) | 3.9 ± 0.5 (9) |
| 1,25-(OH)$_2$D$_3$ (125 ng) | 145.2 ± 47.8 (8) | 5.2 ± 0.5 (7) |
|  | $p < 0.005$ | $p < 0.001$ |
| compound I (500 ng) | 110.0 ± 20.7 (7) | 4.9 ± 0.5 (8) |
|  | $p < 0.01$ | $p < 0.005$ |

What is claimed is:

1. Compounds having the formula

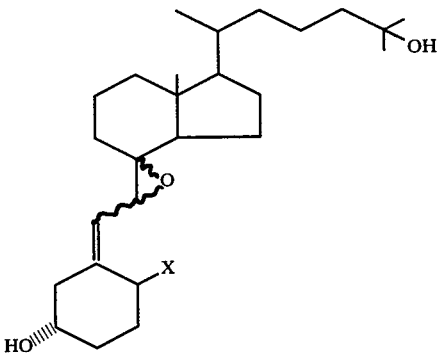

where X is a group selected from keto or hydroxy.

2. A compound having the formula

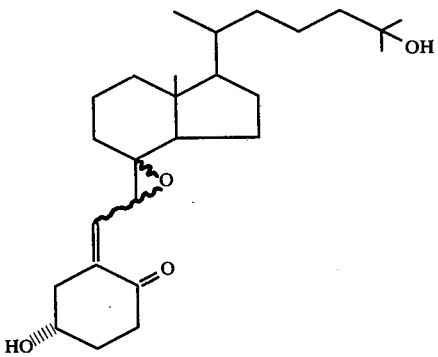

* * * * *